US00PP12263P2

(12) United States Plant Patent
Sorensen

(10) Patent No.: US PP12,263 P2
(45) Date of Patent: Dec. 11, 2001

(54) OSTEOSPERMUM PLANT NAMED 'AKSILLO'

(75) Inventor: Carl Aksel Kragh Sorensen, Aabyhoj (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/422,169

(22) Filed: Oct. 22, 1999

(51) Int. Cl.[7] ..... A01H 5/00

(52) U.S. Cl. ..... Plt./360
(58) Field of Search ..... Plt./360

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of *Osteospermum* plant named 'Aksillo', characterized by its compact, mounding and spreading plant habit; freely flowering habit with numerous inflorescences per plant; spoon-shaped white ray florets with blue purple lower surfaces and blue purple disc florets; and good high temperature tolerance.

1 Drawing Sheet

BACKGROUND OF THE INVENTION

The present invention relates to a new and distinct cultivar of Osteospermum plant, botanically known as *Osteospermum ecklonis*, and hereinafter referred to by the cultivar named Aksillo.

The new Osteospermum was discovered by the Inventor in a controlled environment in Aabyhoj, Denmark, in 1996, as a naturally-occurring mutation of *Osteospermum ecklonis* 'Cape Daisy Nairobi', disclosed in U.S. Plant Pat. No. 10,340. The new Osteospermum was observed as a single plant in a group of flowering plants of the parent cultivar. The selection of this plant was based on its unique ray floret shape. Plants of the new Osteospermum have spoon-shaped ray florets whereas plants of the cultivar Cape Daisy Nairobi have flat, ligulate ray florets.

Asexual propagation of the new cultivar by terminal cuttings at Aabyhoj, has shown that the unique features of this new Osteospermum are stable and reproduced true to type in successive generations.

SUMMARY OF THE INVENTION

The following traits have been repeatedly observed and are determined to be the unique characteristics of 'Aksillo'. These characteristics in combination distinguish 'Aksillo' as a new and distinct cultivar:

1. Compact, mounding and spreading plant habit.

2. Freely flowering with numerous inflorescences per plant.

3. Spoon-shaped white ray florets with blue purple lower surfaces and blue purple disc florets.

4. Good high temperature tolerance.

The new cultivar can be compared to the Osteospermum cultivar Cape Daisy Namaqua, disclosed in U.S. Plant Pat. No. 10,491. In side-by-side comparisons conducted in Encinitas, Calif., plants of the new cultivar differ from plants of the cultivar Cape Daisy Namaqua in the following characteristics:

1. Plants of the new Osteospermum are more compact and more spreading (less upright) than plants of the cultivar Cape Daisy Namaqua.

2. Plants of the new Osteospermum have shorter internodes and more leaves than plants of the cultivar Cape Daisy Namaqua and are therefore denser and bushier.

3. Foliage of plants of the new Osteospermum is not fragrant whereas foliage of plants of the cultivar Cape Daisy Namaqua has a spicy fragrance.

4. Plants of the new Osteospermum are more freely flowering, especially during the summer, than plants of the cultivar Cape Daisy Namaqua.

5. Plants of the new Osteospermum have slightly larger inflorescensces than plants of the cultivar Cape Daisy Namaqua.

6. Plants of the new Osteospermum have shorter peduncles than plants of the cultivar Cape Daisy Namaqua.

7. Ray florets of plants of the new Osteospermum have a more pronounced spoon-shape than ray florets of plants of the cultivar Cape Daisy Namaqua.

The cultivar Aksillo has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph as the top of the sheet comprises a side perspective view of a typical flowering plant of 'Aksillo'.

The photograph at the bottom of the sheet is a close-up view of typical inflorescence buds, individual ray florets, inflorescences and leaves of 'Aksillo' (left) and 'Cape Daisy Namaqua' (right). Foliage and floret colors in the photographs may appear different from the actual colors due to light reflectance.

DETAILED BOTANICAL DESCRIPTION

The following observations, meassurements and values describe plants of the new cultivar grown in Encinitas, Calif., during the spring in a polyethylene-covered greenhouse. During the production period, day temperatures ranged from 16 to 21° C., night temperatures ranged from 10 to 16° C., and light levels were about 4,000 foot-candles. Plants were pinched (terminal apex removed) one time. Measurements and numerical values represent averages for typical flowering plants grown in one-gallon containers with two plants per container; plants used for descriptions and the photographs were about 19 weeks old.

Color references are made to The Royal Horticultural Society Colour Chart except where general terms of ordinary dictionary significance are used.

Botanical classification: *Osteospermum ecklonis* cultivar Aksillo.

Parentage: Naturally-occurring mutation of *Osteospermum ecklonis* cultivar Cape Daisy Nairobi, disclosed in U.S. Plant Pat. No. 10,340.

Propagation:

*Type.*—By terminal cuttings.

*Time to initiate roots.*—About 13 days at 18° C.

*Time to develop roots.*—About 26 days at 18° C.

*Root description.*—Fibrous.

Plant description:

*Appearance.*—Perennial herbaceous container and garden plant. Round and mounded plant habit; spreading. Freely branching, about 14 lateral branches developing after pinching; dense and bushy.

*Crop time.*—From planting rooted cuttings, about 14 to 19 weeks are required to produce a finished, flowering plant in a one-gallon container.

*Vigor.*—Moderate.

*Plant height, to top of inflorescence plane.*—About 18 cm.

*Plant spread.*—To outer leaves, about 20 cm; to outer inflorescences, about 31 cm.

*Lateral branch description.*—Length: About 13 cm. Diameter: About 4 mm. Internode length: About 1 cm. Texture: Sparsely pubescent; woody at base. Color: 146B to 146C.

*Foliage description.*—Leaves alternate, single. Length, fully expanded leaves, basal: About 4.5 cm. Width, fully expanded leaves, basal: About 8 mm. Shape: Elliptic. Apex: Acute. Base: Attenuate, sessile. Margin: Entire. Aspect: Mostly flat. Texture: Somewhat coarse, glandular. Fragrance: Not detected. Color: Young foliage, upper surface: Slightly darker than 146A. Young foliage, lower surface: 146A. Fully expanded foliage, upper surface: 139A. Fully expanded foliage, lower surface: 137A. Attenuated leaf base: 139B. Venation, upper and lower surfaces: 137A.

Inflorescence description:

*Appearance.*—Daisy-type composite inflorescence form; actinomorphic. Single inflorescences displayed above or beyond foliage, upright to horizontal on long peduncles arising from leaf axils. Disc and ray florets arranged acropetally on a capitulum. Freely flowering, typically about 90 opened and opening inflorescences per plant. Inflorescences last about one week. Inflorescences persistent.

*Flowering response.*—Plants flower continuously from April to October in the Northern Hemisphere.

*Fragrance.*—None detected.

*Inflorescence size.*—Diameter: About 5.5 cm. Depth (height): About 1.4 cm. Diameter of disc: About 1.4 cm.

*Inflorescence buds (at stage of showing color).*—Length: About 1.8 cm. Width: Abou 1.4 cm. Shape: Ovoid. Color: 144A to 83C.

*Ray florets.*—Length: About 2.5 cm. Width: Towards base, about 5 mm; midsection, at indentation, about 3 mm; towards apex, 4 mm. Shape: Spoon. Apex: Broadly acute. Base: Attenuate. Margin: Entire. Aspect: Horizontal. Texture: Smooth, velvety. Number of ray florets per inflorescence: About 22 in a single whorl. Color: When opening, upper surface: Base, 155C; apex, 146B. When opening, lower surface: 79B. Fully opened, upper surface: 155D. Fully opened, lower surface: Base, 85A; apex, 86A.

*Disc florets.*—Shape: Tubular; five-lobed, fluted at apex. Number of disc florets per inflorescnece: Numerous, about 82. Length: About 9 mm. Width: About 2 mm. Color: Immature: Base, 142D; apex, 86A. Mature: Base, 85D; apex, 86A.

*Phyllaries.*—Shape: Ligulate. Length: 1.8 cm. Apex: Sharply acute. Margin: Entire, membranous edges. Quantity and arrangement: About 16 in a single whorl. Color, upper and lower surfaces: 146A.

*Peduncle.*—Length: Terminal peduncle, about 7 cm; third peduncle, about 5 cm. Aspect: Moderately strong; inflorescences held above foliage. Primary peduncles, erect; secondary peduncles, about 45° to vertical. Texture: Slightly coarse; glandular. Color: 144A.

*Reproductive organs.*—Androecium: Present on disc florets only. Stamens: Five. Anther shape: Elongated, oblong. Anther length: About 3 mm. Anther color: 83A. Pollen amount: Scarce. Pollen color: 23B. Gynoecium: Present on ray and disc florets. Pistils: One. Pistil length: Abou 9 mm. Stigma shape: Bipartite. Stigma color: 83A. Style length: About 5 mm. Style color: 145D. Ovary color: 145C.

*Seed.*—Seed development has not been observed.

Disease resistance: Resistance to pathogens common to Osteospermum has not been observed on plants of the new Osteospermum.

It is claimed:

1. A new and distinct cultivar of Osteospermum plant named 'Aksillo', as illustrated and described.

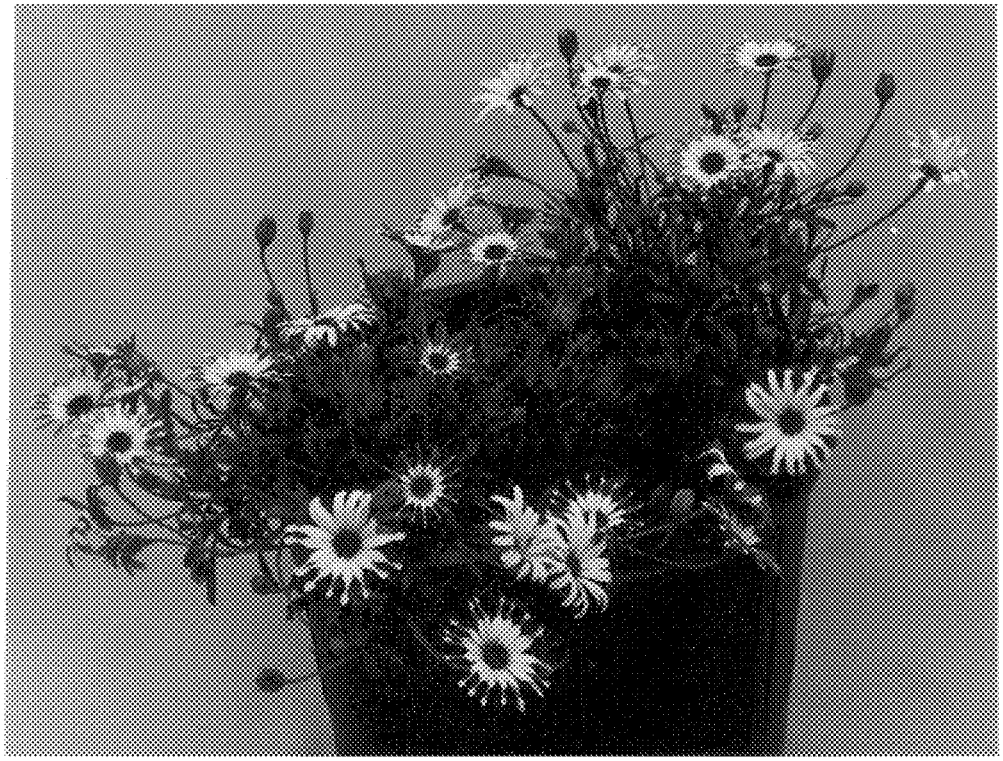
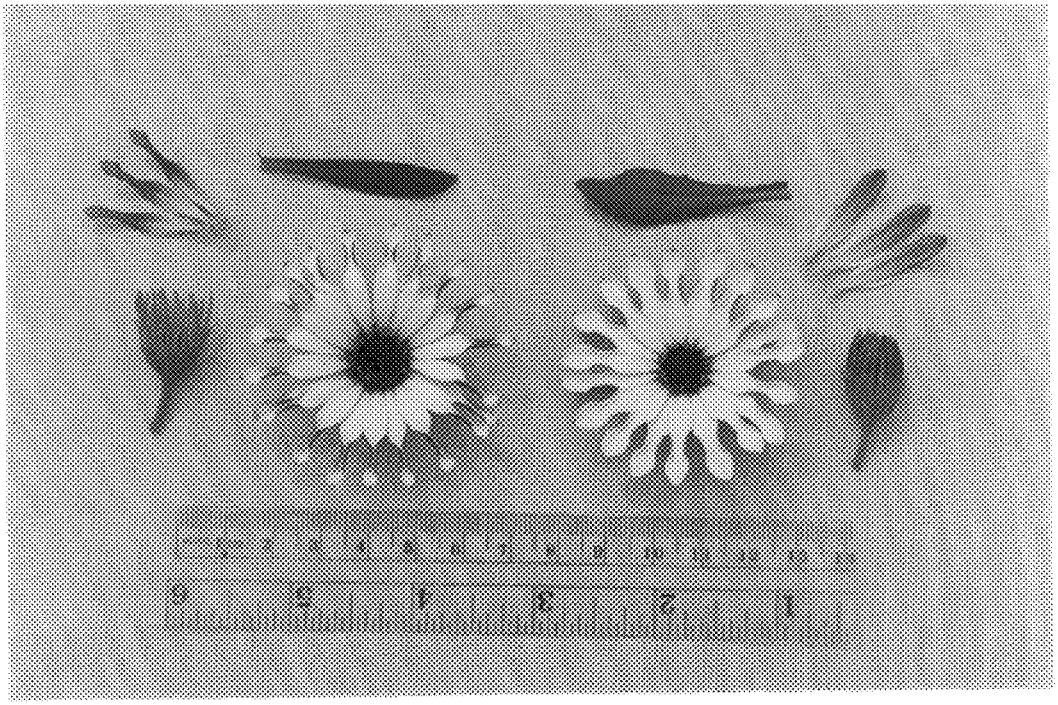

* * * * *